(12) United States Patent
Reid, Jr. et al.

(10) Patent No.: US 6,830,582 B1
(45) Date of Patent: Dec. 14, 2004

(54) THERMAL WRAP FOR BODY MEMBER

(75) Inventors: Lawrence G. Reid, Jr., Germanton, NC (US); Stanley S. Budzinski, Addison, IL (US)

(73) Assignee: Zilon Corporation, Rural Hall, NC (US)

(*) Notice: Subject to any disclaimer, the term of this patent is extended or adjusted under 35 U.S.C. 154(b) by 133 days.

(21) Appl. No.: 10/075,423

(22) Filed: Feb. 13, 2002

Related U.S. Application Data (60) Provisional application No. 60/268,463, filed on Feb. 13, 2001.

(51) Int. Cl.[7] ................................. A61F 7/08; A61F 7/10
(52) U.S. Cl. ........................... 607/112; 607/114; 601/15
(58) Field of Search ........................... 667/96, 108, 112, 667/114; 601/15

(56) References Cited

U.S. PATENT DOCUMENTS

| 4,207,885 A | 6/1980 | Hampton et al. |
| 4,347,848 A | 9/1982 | Hubbard et al. |
| 4,756,311 A * | 7/1988 | Francis ........................ 607/114 |
| 5,052,387 A | 10/1991 | Natali |
| 5,641,325 A | 6/1997 | Delk et al. |
| 2002/0073731 A1 * | 6/2002 | Bride-Flynn ................. 62/530 |

* cited by examiner

*Primary Examiner*—Danton DeMille
(74) *Attorney, Agent, or Firm*—Kilpatrick Stockton LLP (57) ABSTRACT

This invention relates to a therapeutic bag for use in hot or cold treatment therapy of injuries. The therapeutic bag comprises a chamber comprising a mouth and an interior containment pocket; a sealing mechanism fixedly attached to the chamber for sealing the interior containment pocket closed in a substantially leak-proof manner, and an attachment mechanism fixedly attached to the therapeutic bag for positioning and holding the chamber in a desired location. Also disclosed are methods of manufacturing the therapeutic bag and methods for using the therapeutic bag in a treatment protocol.

1 Claim, 4 Drawing Sheets

THERMAL WRAP FOR BODY MEMBER

CROSS-REFERENCE TO RELATED APPLICATIONS

This application claims priority to Applicants' co-pending provisional application, entitled "Reusable Ice Bag and Method of Manufacture", U.S. Ser. No. 60/268,463, filed Feb. 13, 2001, the disclosure of which is hereby incorporated herein by reference.

FIELD OF THE INVENTION

The present invention relates generally to an apparatus for holding a cold or warm material for therapeutic uses, treatment methods using the apparatus, and methods of producing the apparatus. Included among the embodiments of the present invention are embodiments comprising a chamber, a sealing mechanism and an attachment mechanism so that the bag may be positioned adjacent to an area of the body to treat injury and relieve associated pain. The chamber may hold a cold material such as ice, or a hot material, such as a heating composition.

BACKGROUND OF THE INVENTION

Ice and heat therapy is used extensively within the health care community to treat injury and relieve associated pain. The therapy is typically administered via a bag containing ice or another cooling or heating substance. These bags generally have a hollow chamber or pocket, a neck, and a mouth. The hollow chamber or pocket may be formed from a single or multi-layer laminated plastic film, which may be laminated to a fabric or non-woven material for insulation. Clips may be used at the neck area to close and seal the mouth to prevent it from leaking. Preferably, the mouth of the bag is as large as possible to facilitate easy filling of the bag.

Clip designs for sealing the bag shut may vary, but all pose a problem as they have a tendency to interfere when a bag is filled at, for example, an ice machine. The clips are also prone to falling off when an bag is opened. Due to the cost of manufacturing large clips, as well as their operational inefficiency, the mouth of a typical bag is generally relatively small. For example, hinged clips having a blade, a trough, and an attachment at one end, are prone to leaks at the center-section of the clip as the clip becomes larger because there is no structural support in the center area of these clips. Roll clamps, consisting of a male and a female section which are secure across the clamp, provide better sealing properties. However, roll clamps are expensive and may be difficult to close. Additionally, clips are typically taped to a bag so that they remain with the bag when not in use. Condensation, however, may detach the tape, causing a clip to be lost. Finally, clips may have sharp edges, and a health care worker or patient may experience discomfort or injury as the result of a sharp edge coming into contact with their skin.

Bags holding cold or warm materials are typically held in place relative to an injured area of the body with straps attached to the corners of the bag. Rigid or stretch wraps may also be used to hold a bag in place, however, these wraps are typically not fixedly attached to the bag.

Thus, what is needed are reusable bags that have low cost and effective sealing mechanisms fixedly attached thereto, large mouths to facilitate easy filling, and attached straps or wraps for positioning and holding the bag relative to an injured area of the body.

SUMMARY OF THE INVENTION

Accordingly, the above identified shortcomings of existing therapeutic bags are overcome by the present invention, which relates to therapeutic bags having a low cost and effective sealing mechanism, a large mouth to facilitate easy filling, and attached straps or wraps for positioning and holding the bag relative to an injured area of the body. In embodiments of the present invention, bags may be advantageously utilized to hold a cold substance, such as ice or a hot substance, such as a heated chemical composition.

In an embodiment, the present invention provides a therapeutic bag for treating injury and relieving associated pain comprising:

a chamber having a mouth and an interior containment pocket;
   a mechanism for retaining a material in the chamber; and an attachment mechanism fixedly attached to the therapeutic bag for positioning and holding the chamber in a desired location. The mechanism for retaining a material in the chamber may comprise a sealing mechanism fixedly attached to the chamber for sealing the interior containment pocket closed in a substantially leak-proof manner.

The present invention also relates to methods of making the aforementioned therapeutic bags. The therapeutic bags of the present invention can be easily modified to be made of virtually any kind of suitable material for holding a cool or warm material. The attached straps or wraps can likewise be made of virtually any kind of suitable material and/or attachment mechanisms that are capable of holding the bag in position once it is properly positioned on a body. Furthermore, the therapeutic bags of the present invention can be modified to be of any suitable size and configuration so as to be useful for application to many different body parts.

For ease of reference in explaining the present invention, embodiments of the present invention are generally described herein with reference to ice. As will be appreciated by those of ordinary skill in the art, embodiments of the present invention are capable of holding different types of cold material, including, but not limited to: frozen water, other frozen liquid compositions, cooled liquid compositions, cooled polymer compositions, cooled mineral materials, cooled metal materials, re-freezable liquid containing vessels, and/or combinations thereof. For example, particular embodiments of the present invention may be designed to hold the commonly available chemical "ice" compositions that are capable of being refrozen. In general, for therapeutic application of cold, an embodiment of the present invention will be capable of holding a material that is below ambient temperature, for example, between −5 and 15 C.

As described above, embodiments of the present invention may also be utilized to hold a "hot" material for therapeutic use in application of heat. Hot materials include, but are not limited to, heated liquid compositions, heated chemical compositions, heated mineral materials, heated metal materials and/or combinations thereof. In general, for the therapeutic application of heat, the material will have an initial temperature that is above ambient temperature, for example above 22 C, including 23–50 C. Prior to application to an injured area, the heated material should be at a temperature below a temperature that will damage tissue or cause pain to a user.

As used herein, ambient temperature refers to a temperature of 18–25 C.

In certain embodiments of the present invention, the chamber may comprise a sealing mechanism to retain the hot or cold material within the chamber. In other possible embodiments of the present invention, the chamber may be designed to retain a hot or cold material without a sealing mechanism. For example, an embodiment of the present invention may comprise a chamber suitable for retaining a commercially available chemical cold or hot pack. In these types of chemical packs, the chemical substance is retained within the pack by a substantially leak proof barrier. Thus, in this type of embodiment of the present invention, the chamber may be designed to hold the chemical pack, but need not necessarily include a separate sealing mechanism.

The present invention also relates to methods of using a therapeutic bag of the present invention for treating injury and relieving associated pain. A method of the present invention comprises positioning a therapeutic bag of the present invention in proximity to an area to be treated and securing the therapeutic bag utilizing the attachment mechanism provided as part of the therapeutic bag. In an additional preliminary step, a method of the present invention may further comprise filling the therapeutic bag with a cold material or a hot material. In an additional subsequent step, a method of the present invention may further comprise leaving the bag in place until the hot or cold material reach, or near, ambient temperature.

The foregoing description of the present invention is provided by way of an example only. As is understood by those skilled in the art, the concepts discussed herein may be implemented in a variety of ways. Each is intended to be within the purview and scope of the present invention. Further aspects and advantages of the present invention will be more readily apparent to those skilled in the art during the course of the following description, references being made to the accompanying drawings which illustrate some preferred forms of the present invention and wherein like characters of reference designate like parts throughout the drawings.

DETAILED DESCRIPTION OF THE INVENTION

Accordingly, the above identified shortcomings of existing therapeutic bags are overcome by the present invention, which relates to reusable bags having a low cost and effective sealing mechanism fixedly attached thereto, a large mouth to facilitate easy filling, and attached straps or wraps for positioning and holding the bag relative to an injured area of the body. In embodiments of the present invention, bags may be advantageously utilized to hold a cold substance, such as ice.

The present invention also relates to methods of making the aforementioned therapeutic bags. The therapeutic bags of the present invention can be easily modified to be made of virtually any kind of suitable material for holding a cool or warm material. The attached straps or wraps can likewise be made of virtually any kind of suitable material and/or attachment mechanisms that are capable of holding the bag in position once it is properly positioned on a body. Furthermore, the therapeutic bags of the present invention can be modified to be of any suitable size and configuration so as to be useful for application to many different body parts.

One embodiment of the present invention discloses a reusable therapeutic bag for treating injury and relieving associated pain. This therapeutic bag includes a chamber with a mouth and an interior containment pocket, a mechanism for retaining a material within the interior containment pocket, and an attachment mechanism attached to the bag for positioning and holding the therapeutic bag in a desired location. The mechanism for retaining a material within the interior containment pocket may comprise a sealing mechanism fixedly attached to the chamber for sealing the interior containment pocket closed in a substantially leak-proof manner in an embodiment of the present invention advantageous for use with ice, or ice cubes, the chamber comprises a chamber suitable for retaining liquid as the ice melts, for example a substantially waterproof bag.

The sealing mechanism of the therapeutic bag may be a ZIPLOCK®-type closure seal, or other suitable resealable sealing mechanism. This ZIPLOCK®-type closure seal is preferably attached to the interior containment pocket of the bag near the mouth of the chamber.

In an embodiment, the therapeutic bags of the present invention comprise two walls, each having two side edges, a top edge and a bottom edge. The two walls are joined together along their two side edges and their bottom edges to form an interior chamber, while their top edges remain unattached to form a mouth for filling the chamber. The two walls may be heat sealed together, along at least two of their edges, but may also be sealed together in any other suitable way, such as by using adhesives, bonding, folding, etc. The walls of this ice bag may be a single layer thick, or they may be multiple layers thick. For example, a waterproof inner layer may be attached to an insulating outer layer. Additional layers, such as one or more middle layers, may also be added to each wall as desired for a given application. These layers may be laminated together, or they may be joined via adhesives or other suitable joining methods. One embodiment of the present invention is an therapeutic bag comprising triple layer walls, where each wall has an outer layer made of non-woven polypropylene, a middle layer made of nylon, and an inner layer made of white linear low-density polyethylene.

Various attachment mechanisms can be attached to the therapeutic bags of the present invention, such as tie strings, and rigid or stretchy wraps. These attachment mechanisms may be attached to the therapeutic bag in any suitable manner, but are preferably attached via heat sealing or stitching.

In one embodiment of the present invention, two pairs of tie strings are attached to the therapeutic bag, one pair near each end of the therapeutic bag. While these tie strings are depicted as projecting basically perpendicularly out from the side edges of the bag, it should be obvious to one skilled in the art that these tie strings could also be attached in a variety of other positions and locations without deviating from the scope of this invention. For example, the tie strings could be attached along the side edges of the therapeutic bag so that they extend in a basically parallel manner out from the side edges of the bag. These tie strings can be of any length, but should at least be long enough to be wrapped and tied around a portion of a person's body so that the bag can be held securely in place.

Another embodiment of the present invention includes a wrap as the attachment mechanism. A suitable wrap comprises a stretchy woven elastic compression bandage and may be attached to the outside of the therapeutic bag so that the wrap extends outwardly from the ice bag substantially parallel to the side edges of the therapeutic bag. However, the wrap may be made of any other suitable material, and may be attached to the therapeutic bag at any other suitable location and in any other suitable position. This wrap can be of any length, but should at least be long enough to be wrapped and secured around a portion of a person's body so that the therapeutic bag can be held securely in place.

One embodiment of the present invention comprises a hook-type fastening mechanism on the wrap so that the wrap can be easily secured in its desired location. While both a hook portion and a loop portion of a hook-and-loop type fastener can be provided, in this embodiment, the ¢ hook portion attaches directly to the fabric wrap at any location, so the loop portion is not necessary.

A method of making a therapeutic bag of the present invention comprises providing two walls of material, each wall having four edges, an inside surface and an outside surface, and also providing a closure or sealing mechanism and an attachment mechanism. The two walls of material are placed together with their respective inside surfaces facing one another, and then at least three of their respective edges are joined together to form a pocket. The fourth of the respective edges of these two wall are left un-joined to form a mouth. The closure mechanism is preferably joined to the inside surfaces of the two walls of material near the mouth. An attachment mechanism can also be attached to the pocket or to another portion of the therapeutic bag.

In one embodiment of the present invention, the closure mechanism is a ZIPLOCK®-type closure seal that is joined to the inside surfaces of the two walls of material via beat sealing, gluing and/or bonding, or any other suitable joining method. The two walls of the material may be joined together along at least three of their respective edges via heat sealing, gluing, folding and/or bonding, or any other suitable joining method. The attachment mechanism may be attached to the therapeutic bag via heat sealing, gluing, bonding and/or stitching, or any other suitable attachment method.

Another method of making an therapeutic bag of the present invention includes providing a layer of non-woven polypropylene, a layer of nylon, a layer of white linear low-density polyethylene, a closure mechanism, and an attachment mechanism. The layer of non-woven polypropylene may be laminated to the layer of nylon to form a double layered section. The layer of white linear low-density polyethylene can then be laminated to the layer of nylon on the double layered section to form a triple layered section. The closure mechanism can be placed between two of the triple layered sections, where the two triple layered sections have layers facing one another, and then the closure mechanism can be joined to the two triple layered sections, and the two triple layered sections can be joined together to form a bag. The attachment mechanism can then be attached to the bag.

The present invention also relates to methods of using a therapeutic bag of the present invention for treating injury and relieving associated pain. A method of the present invention comprises positioning a therapeutic bag of the present invention in proximity to an area to be treated and securing the therapeutic bag utilizing the attachment mechanism provided as part of the therapeutic bag. In an additional preliminary step, a method of the present invention may further comprise filling the therapeutic bag with a cold material or a hot material. In an additional subsequent step, a method of the present invention may further comprise leaving the bag in place until the hot or cold material reach, or near, ambient temperature.

An embodiment of a method of using a therapeutic bag of the present invention for treating injury and relieving associated pain comprises providing an ice bag that has a waterproof bag with a mouth and an interior containment pocket, a sealing mechanism, and an attachment mechanism. A cooling substance may be introduced into the interior containment pocket of the waterproof bag via the mouth of the waterproof bag. The waterproof bag may then be sealed closed with a sealing mechanism, such as a ZIPLOCK®-type closure seal. The ice bag may then be positioned in its desired location on a person's body, on the area needing treatment. The ice bag may be positioned anywhere on a person's body, such as on their arms, wrists, legs, knees, ankles, torsos, head, neck, feet, hands, etc. Finally, the ice bag may be secured in place by an attachment mechanism, such as one or more pairs of tie strings or an attachment wrap. The tie strings should be long enough to be wrapped around a portion of a person's body and tied to secure the ice bag in position. The attachment wrap should be long enough to be wrapped around a portion of a person's body and fastened to secure the ice bag in position. The attachment wrap may be a stretchy woven elastic compression bandage that is fastened by a hook-and-loop type fastener, or other suitable fastening means.

The foregoing description of the present invention is provided by way of an example only. As is understood by those skilled in the art, the concepts discussed herein may be implemented in a variety of ways. Each is intended to be within the purview and scope of the present invention. Further aspects and advantages of the present invention will be more readily apparent to those skilled in the art during the course of the following description, references being made to the accompanying drawings which illustrate some preferred forms of the present invention and wherein like characters of reference designate like parts throughout the drawings.

For the purposes of promoting an understanding of the principles of the invention, references will now be made to some of the preferred embodiments of the present invention as illustrated in FIGS. 1–5, and specific language used to describe the same. For illustrative purposes, the invention is primarily shown and described as applied to ice bags for use on a person's arms and legs, but as will be readily apparent, the invention can be easily adapted for use anywhere else on a person's body, and can also be adapted to hold any type of cooling substance such as, for example, another solid or even a liquid.

Figure 1:
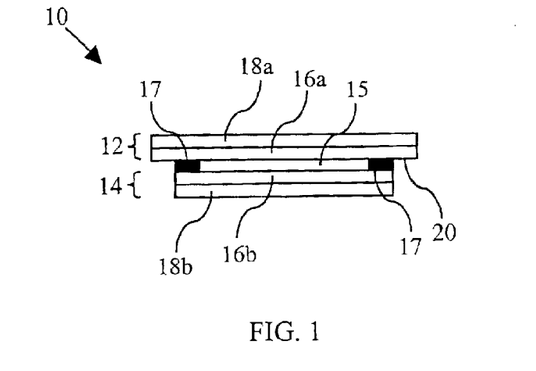
FIG. 1 is a cross-sectional view of one embodiment of the ice bag of the present invention showing the interior containment pocket between the double-ply walls of the ice bag, an overhang along the sides of the bag, and insulating outer layers attached to the outer surfaces of the walls of the bag.

Referring now to FIG. 1, one embodiment of the therapeutic bag 10 of the present invention includes a first or back wall 12 and a second or front wall 14 sealingly attached to one another 17 such that the first wall 12 and the second wall 14 form a hollow chamber or interior containment pocket 15, which may be substantially waterproof. Each of the walls 12, 14 may comprise a double thick layer comprising at least a waterproof inner layer 16a, 16b laminated to an insulating outer layer 18a, 18b. However, it is also possible that only one wall, or no walls, will have an insulating outer layer attached thereto, and will therefore be only a single layer thick. Additionally, walls 12, 14 may be comprised of three or more layers, such as a layer of non-woven polypropylene on the outside of the ice bag, attached to a middle layer of nylon, which is then attached to a layer of white linear low-density polyethylene on the inside surface of the ice bag. Furthermore, suitable attachment methods other than lamination may be used to attach the insulating outer layer to the inner layer, such as glue, adhesives, and the like.

Wall 12 comprises a top edge 46, two side edges 47a, 47b, and a bottom edge 50, as well as an inside surface and an outside surface. Wall 14 also comprises a top edge 48, two side edges, and a bottom edge 50, as well as an inside surface and an outside surface. In one embodiment of the present invention, the first wall 12 may be attached to the second wall 14 on three of the four edges via a heat seal or other suitable seal, leaving one open unattached edge to provide a mouth 36 for filling. In another embodiment, a single piece of material may be folded approximately in half to form first wall 12 and second wall 14 so that they are foldably connected to one another along one edge (i.e., along bottom edge 50), then the two side edges can be sealed together by any suitable means such as heat sealing or the like, leaving one open unattached edge to provide a mouth 36 for filling. Ice, or any other suitable cooling substance, may be introduced, via mouth 36, to the watertight container or bag 15 formed between walls 12 and 14.

One wall (i.e., first wall 12) may have larger dimensions than the other wall (i.e., second wall 14) such that there is an overhang 20 on one or more sides. For example, overhang 20 is shown on the sides in FIG. 1, and at the top in FIG. 2. This overhang 20 results in a portion of the inner layer 16a of the first wall 12 being exposed. Straps or a rigid or stretch wrap may then be attached to this exposed, heat-sealable overhang area 20. Alternatively, the straps or other attachment mechanism may be otherwise suitably attached to therapeutic bag 10, such as by gluing, fusing, bonding, sewing, stitching, and the like.

Figure 2:
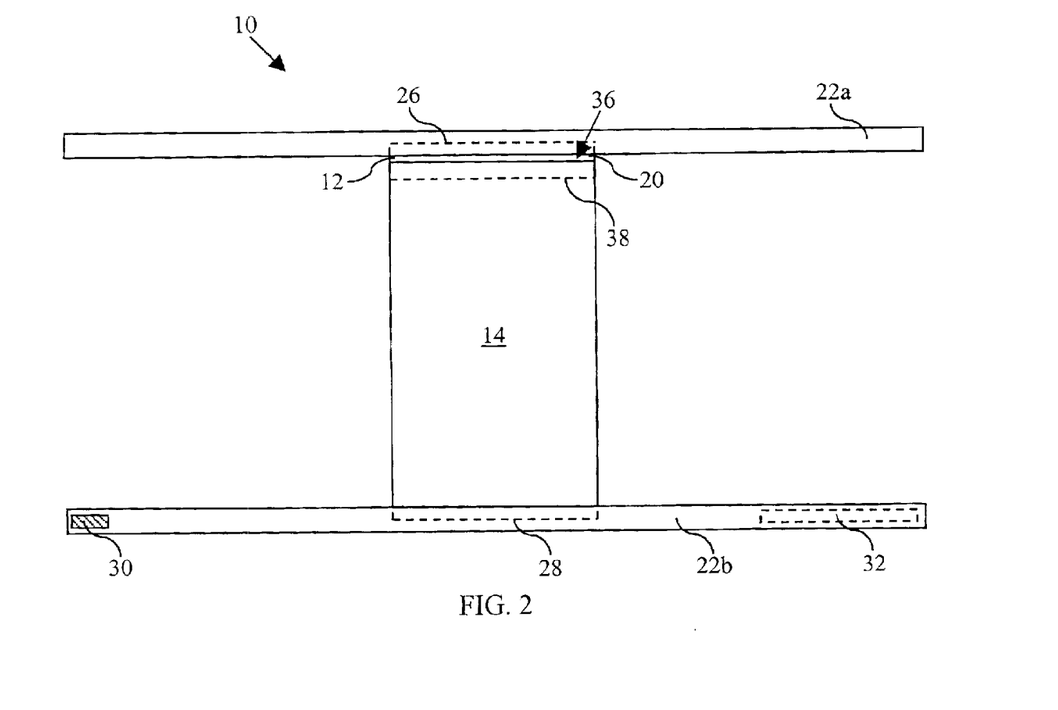
FIG. 2 is a top view of another embodiment of the ice bag of the present invention showing tie-wrap straps fixedly attached to the ice bag.

Referring now to FIG. 2, there is shown one embodiment of the present invention that includes tieable straps 22a, 22b as the attachment mechanism. The straps 22a, 22b may be constructed of a rigid or stretchy material, or any material suitable for tying purposes. Straps 22a, 22b may be knitted, woven, non-woven, etc. In this embodiment, the straps 22a, 22b are fixedly attached to two opposing ends 26, 28 of ice bag 10. As an alternative to tying the straps, one side of the first end of a strap 22b may include a hook-type fastener 30 and the opposite side of the second end of that strap 22b may include a fabric or other loop material 32 for receiving and securing the hook-type fastener 30. The straps 22a, 22b may also be closed, continuous loops (not shown) made of, for example, an elastic material that can be slipped onto, or over, an area of the body, effectively positioning the ice bag 10 for therapeutic purposes.

Figure 3:
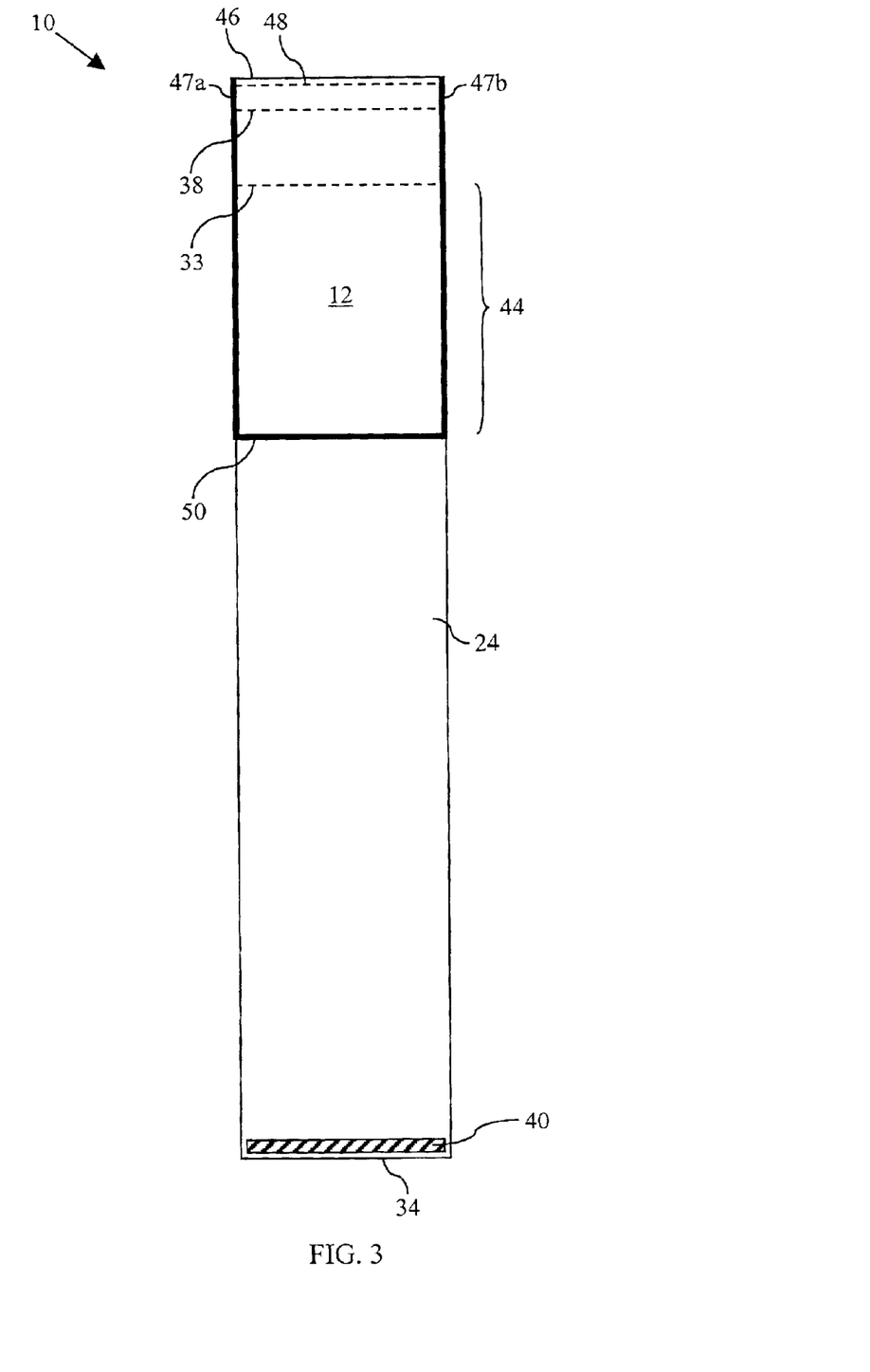
FIG. 3 is a bottom view of another embodiment of the ice bag of the present invention showing the back wall, a fabric stretch wrap, and a hook-and-loop type attachment mechanism fixedly attached to the fabric stretch wrap.
Figure 4:
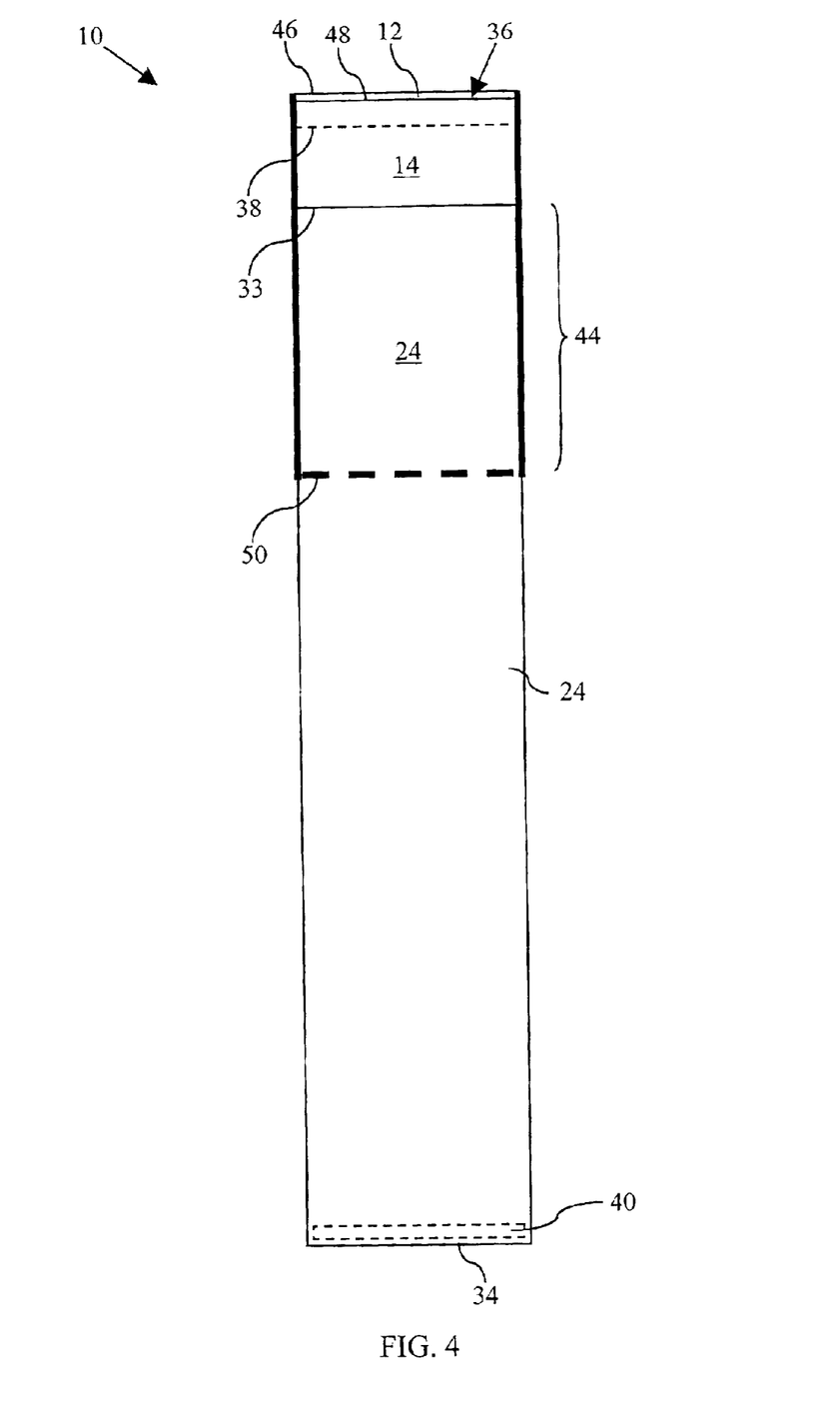
FIG. 4 is a top view of the ice bag shown in FIG. 3 showing the fabric stretch wrap attached to the front wall and also showing a ZIPLOCK®-type sealing mechanism.

Referring now to FIGS. 3 and 4, another embodiment of this invention shows that stretch or rigid wrap 24 may be attached to ice bag 10 for holding and securing the therapeutic bag in its desired position. Any suitable materials may be used for wrap 24. However, preferably, this wrap 24 is a stretchy woven elastic compression bandage as disclosed in our U.S. Pat. No. 4,207,885 (issued Jun. 17, 1980 to Hampton et al.), hereby incorporated in full by reference. The remaining sides of bag 10 may be operable for receiving the free end 34 of wrap 24. Alternatively or additionally, the central portion of ice bag 10 may also be operable for receiving the free end 34 of wrap 24. The free end 34 of wrap 24 may also, or additionally, include a hook-type fastener 40, and the wrap 24 may include a fabric or other loop for receiving the hook, either on the other end or elsewhere on the wrap 24. As shown in the embodiment depicted in FIGS. 3 and 4, the hook-type fastener 40 attaches directly to fabric wrap 24, in any location thereon. This allows the bag to be wrapped around a variety of different sized arms, legs, etc. and still be able to be fastened securely in place. The wrap 24 may also form a closed loop (not shown) made of, for example, an elastic material that may be slipped onto, or over, an area of the body, effectively positioning the bag 10 for therapeutic purposes.

The mouth 36 of bag 10 is sized such that it maybe quickly and easily filled with ice or any other suitable cooling substance. The mouth 36 preferably utilizes a ZIPLOCK®type closure mechanism 38 for sealing bag 10 closed. The closing device 38 should not hinder filling by, for example, an ice machine, and should preferably not be detached from the bag 10 during storage or use. The closing device 38 may be heat-sealed to the inner surfaces of the first wall 12 and the second wall 14. This may be accomplished using suitable sealing and tie-dispensing equipment.

Figure 5:
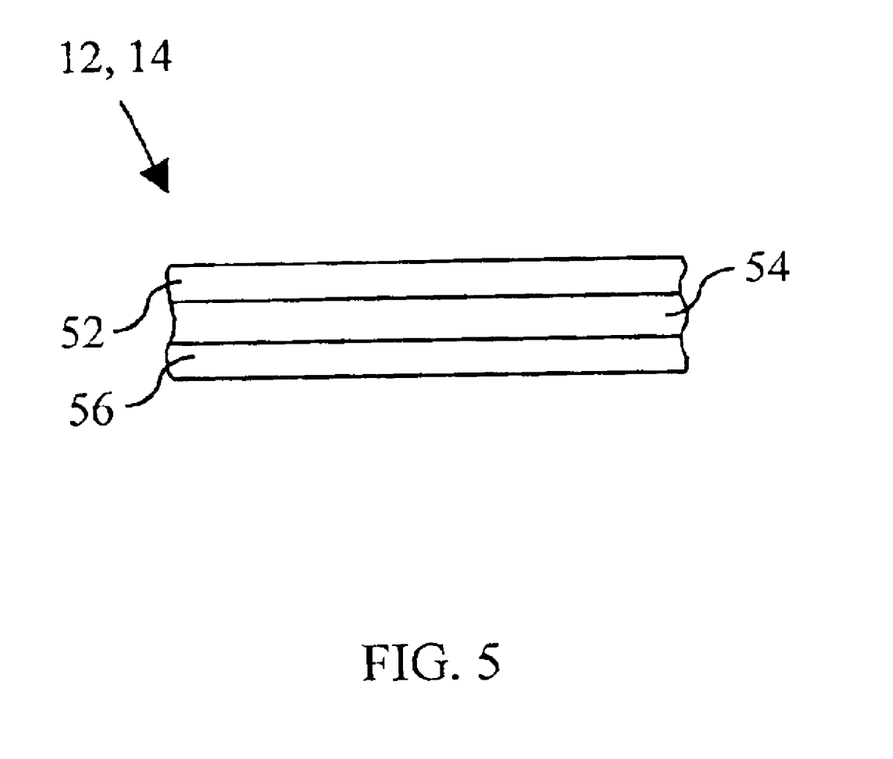
FIG. 5 is a magnified section view of a three layer wall used in one embodiment of the present invention.

Referring now to FIG. 5, each wall 12, 14 of the multi-layer bag 10 of the present invention may be constructed by, for example, laminating a non-woven polypropylene layer 52 to a layer of nylon 54, using poly extrusion or an adhesive. This nylon layer 54 may, in turn, be laminated to a layer of, for example, white linear low-density polyethylene 56, again using poly extrusion or an adhesive. These walls 12, 14 may then be brought together, with their polyethylene layers 56 facing one another to form the inside surface of the bag, with the ZIPLOCK®-type material 38 disposed between the walls 12, 14, and appropriate portions of two or three edges of each wall 12, 14, may then be heat sealed together. Appropriate portions of the ZIPLOCK®-type material 38 are preferably simultaneously heat sealed to the inside surfaces of each wall 12, 14. The desired attachment mechanism may then be attached to the ice bag 10. For example, tieable straps 22a, 22b may be attached to ice bag 10, as shown in FIG. 2, via heat sealing, gluing, adhesives, sewing, or any other suitable technique. Alternatively, wrap 24 may be stitched 44 to the side edges of bag 10, while the top edge 33 and bottom edge 34 are left unattached, as shown in FIGS. 3 and 4.

While the figures and description herein depict only a few embodiments and methods of making the bags of the present invention, it is contemplated that the present invention may be designed in various sizes and shapes for use on various parts of a person's body. For example, the bag can be designed for use on a person's arms, wrists, legs, knees, ankles, torso, head, neck, feet, hands, etc. The bag can also be designed from a variety of different materials, and in a variety of different colors. Furthermore, various attachment techniques may be used to join various elements together, and the order that elements are joined may be varied, without deviating from the spirit of this invention. Therefore, it should be understood that no limitation of the scope of the invention is hereby intended. The terminology used herein is for the purpose of description only, not limitation. Any modifications or variations in the depicted ice bags and the methods of making them, and such further applications of the principles of the invention as illustrated herein, as would normally occur to one skilled in the art, are considered to be within the spirit of this invention. Thus, it is intended that the present invention cover such modifications and variations as come within the scope of the appended claims and their equivalents.

What is claimed is:

1. A therapeutic bag for treating injury and relieving associated pain comprising:

a chamber comprising a first wall of material and a second wall of material, each wall having an inside surface and comprising two side edges, a top edge, and a bottom edge, the first wall and the second wall being joined along their two side edges and their bottom edges to form an interior containment pocket, the top edges being unattached to form a mouth for filling the chamber;

each wall comprising at least an outer layer, a middle layer, and an inner layer;

a mechanism fixedly attached to the inside surfaces of the two walls of material proximate the mouth of the chamber for sealing the interior containment pocket closed in a substantially leak-proof manner for retaining a hot or cold material within the chamber; and an attachment mechanism fixedly attached to the therapeutic bag for positioning and holding the chamber in a desired location, wherein the outer layer comprises non-woven polypropylene, the middle layer comprises nylon, and the inner layer comprises white linear low-density polyethylene.

* * * * *

UNITED STATES PATENT AND TRADEMARK OFFICE
CERTIFICATE OF CORRECTION

PATENT NO. : 6,830,582 B1
DATED : December 14, 2004
INVENTOR(S) : Lawrence G. Reid, Jr. and Stanley S. Budzinski It is certified that error appears in the above-identified patent and that said Letters Patent is hereby corrected as shown below:

<u>Title page, Item [54] and Column 1, line 1</u>,
Title replace "THERMAL WRAP FOR BODY MEMBER" with -- THERAPEUTIC BAG --.

<u>Column 3,</u>
Line 55, replace "scaling" with -- sealing --.

<u>Column 5,</u>
Line 28, delete the cent sign before "hook".
Line 46, replace "beat" with -- heat --.

Signed and Sealed this

Third Day of May, 2005

JON W. DUDAS
*Director of the United States Patent and Trademark Office*